United States Patent [19]

Husain et al.

[11] Patent Number: 5,475,175
[45] Date of Patent: * Dec. 12, 1995

[54] PROCESS FOR THE PRODUCTION OF ALKYLATE GASOLINE FROM FCC LIGHT ALIPHATICS

[75] Inventors: Altaf Husain, Danbury, Conn.; Albin Huss, Jr., Chadds Ford, Pa.; Iraj I. Rahmim, Voorhees, N.J.

[73] Assignee: Mobil Oil Corporation, Fairfax, Va.

[*] Notice: The portion of the term of this patent subsequent to Jan. 5, 2010, has been disclaimed.

[21] Appl. No.: 228,780

[22] Filed: Apr. 18, 1994

Related U.S. Application Data

[63] Continuation-in-part of Ser. No. 83,588, Jun. 30, 1993, abandoned, which is a continuation-in-part of Ser. No. 929,550, Aug. 13, 1992, Pat. No. 5,258,569.

[51] Int. Cl.$^6$ .................................................. C07C 2/56
[52] U.S. Cl. .................... 585/332; 585/315; 585/316; 585/312; 585/331; 585/717; 585/722
[58] Field of Search ........................ 585/315, 316, 585/312, 331, 332, 717, 722

[56] References Cited

U.S. PATENT DOCUMENTS

| | | | |
|---|---|---|---|
| 3,992,466 | 11/1976 | Plank et al. | 260/671 |
| 4,581,474 | 4/1986 | Hutson, Jr. et al. | 568/697 |
| 4,684,757 | 8/1987 | Avidan et al. | 585/331 |
| 4,886,925 | 12/1989 | Harandi | 585/331 |
| 4,891,466 | 1/1990 | Kocal | 585/464 |
| 4,922,048 | 5/1990 | Harandi | 585/310 |
| 4,996,386 | 2/1991 | Hamilton, Jr. et al. | 585/646 |
| 5,001,292 | 3/1991 | Harandi et al. | 585/322 |
| 5,013,329 | 5/1991 | Bell et al. | 44/448 |
| 5,091,590 | 2/1992 | Harandi et al. | 568/697 |
| 5,100,533 | 3/1992 | Le et al. | 208/67 |
| 5,106,389 | 4/1992 | Harandi et al. | 44/449 |
| 5,146,029 | 9/1992 | Bundens et al. | 585/666 |
| 5,157,194 | 10/1992 | Rahmin et al. | 585/671 |
| 5,177,281 | 1/1993 | Haag et al. | 585/666 |
| 5,254,792 | 10/1993 | Hussain et al. | 585/722 |
| 5,258,569 | 11/1993 | Chu et al. | 585/722 |
| 5,326,922 | 7/1994 | Huss, Jr. et al. | 585/722 |

FOREIGN PATENT DOCUMENTS

| | | |
|---|---|---|
| 0026041 | 4/1981 | European Pat. Off. |
| 0247802 | 6/1990 | European Pat. Off. |

Primary Examiner—Asok Pal
Attorney, Agent, or Firm—Alexander J. McKillop; Dennis P. Santini; Laurence P. Hobbes

[57] ABSTRACT

This invention provides a process for upgrading hydrocarbon feedstock comprising the steps of:

(i) recovering a $C_4$-rich aliphatic stream from a catalytic cracking process;

(ii) contacting said $C_4$-rich aliphatic stream with an isomerization catalyst comprising a zeolite sorbing 30 to 55 mg n-hexane at 90° C., 83 torr, and 15 to 40 mg 3-methylpentane at 90° C., 90 torr, per g dry zeolite in the hydrogen form in a first reaction stage to selectively isomerize $C_4$ n-olefins to $C_4$ isoolefins; and (iii) contacting the product stream from said first reaction stage with a solid acid alkylation catalyst selected from the group consisting of MCM-36 and MCM-49, as described herein and zeolites having a Constraint Index of less than or equal to about 2, to produce isoparaffinic alkylate gasoline.

22 Claims, 1 Drawing Sheet

5,475,175

PROCESS FOR THE PRODUCTION OF ALKYLATE GASOLINE FROM FCC LIGHT ALIPHATICS

Cross-Reference to Related Applications

This application is a Continuation-in-Part of application Ser. No. 08/083,588, filed Jun. 30, 1993, now abandoned which is a Continuation-in-Part of application Ser. No. 07/929,550, filed Aug. 13, 1992 now U.S. Pat. No. 5,258,569.

FIELD OF THE INVENTION

This invention relates to a process for producing high octane gasoline blending components from a $C_4$-rich cracked hydrocarbon stream. The invention particularly relates to an integrated process which upgrades an FCC $C_4$ stream to alkylated gasoline while avoiding the capital and operating expense associated with fractionating $C_4$ isomers.

BACKGROUND OF THE INVENTION

Adding shape-selective zeolites such as ZSM-5 to cracking catalysts, e.g. those used in fluidized catalytic cracking (FCC), improves the octane rating of the gasoline boiling range product. But adding these shape-selective zeolites to the FCC process increases light olefins production, particularly the yield of n-butenes. The n-butenes are not, of themselves, a particularly marketable product, and it would be beneficial to upgrade these normal olefins.

Butene exists in four isomers: butene-1, cis-butene-2, its stereo-isomer trans-butene-2, and isobutene. Conversions between the butenes-2 is known as geometric isomerization, whereas that between butene-1 and the butenes-2 is known as position isomerization, double-bond migration, or hydrogen-shift isomerization. The aforementioned three isomers are not branched and are known collectively as normal or n-butenes. Conversion of the n-butenes to isobutene, which is a branched isomer, is widely known as skeletal isomerization.

U.S. Pat. No. 4,581,474 to Hutson, Jr., et al. teaches a combination alkylation-etherification process in which unreacted $C_4$ olefins produced by etherification are contacted with molecular sieves to absorb 2-butenes and the remaining 1-butenes are split so that a first portion is subjected to double bond isomerization and a second portion is subjected to skeletal isomerization to form isobutene for etherification.

U.S. Pat. No. 4,684,757 to Avidan teaches a method for converting an alcohol feed to an etherate and an isoparaffinic alkylate useful as a gasoline blending stocks.

U.S. Pat. No. 4,891,466 to Chou et al. teaches an integrated process which first isomerizes the feed olefin double bonds and then alkylates the isomerized product in the presence of a supported Lewis acid.

U.S. Pat. No. 5,001,292 to Harandi teaches an integrated etherification/oligomerization process for upgrading oxygenates, light olefins, and paraffins to higher molecular weight gasoline blending components.

U.S. Pat. No. 5,013,329 to Bell et al. teaches a process which etherifies n-olefins and i-olefins in sequential reaction zones and then oligomerizes the unreacted light olefins to form useful gasoline components.

U.S. Pat. No. 5,091,590 to Harandi et al. teaches an integrated process for upgrading an olefin feedstock containing a mixture of iso-olefin and linear olefin to produce tertiary-alkyl ether and gasoline components comprising dimerized iso-olefin.

U.S. Pat. No. 5,100,533 to Le et al. teaches a process for upgrading a fresh virgin naphtha by cracking, etherifying the resulting $C_5$-olefins, recovering the etherate, and oligomerizing the unreacted olefins.

U.S. Pat. No. 5,106,389 to Harandi et al. teaches a process for producing alkyl tertiary alkyl ethers and alkylated aromatics useful as high octane gasoline blending stocks.

U.S. Pat. No. 5,258,569 to Chu et al., incorporated herein by reference, teaches alkylation of isoparaffin with olefin in the presence of MCM-36 as catalyst to provide alkylate.

SUMMARY OF THE INVENTION

In accordance with the present invention, high octane gasoline blending components are produced from a feedstock comprising isobutane and linear butenes. In this integrated process a feed containing isobutane and linear butenes is first passed through an olefin isomerization reactor containing a constrained intermediate pore zeolite, e.g., ZSM-35, to isomerize a substantial portion of linear butenes to isobutene with the resulting isobutane/mixed butene passed through an alkylating reactor containing a solid catalyst, such as MCM-36 to produce alkylate.

DESCRIPTION OF THE DRAWING

The FIGURE is a simplified schematic diagram illustrating the major processing steps of a preferred embodiment of the process of the present invention.

DETAILED DESCRIPTION OF THE INVENTION

Figure 1:
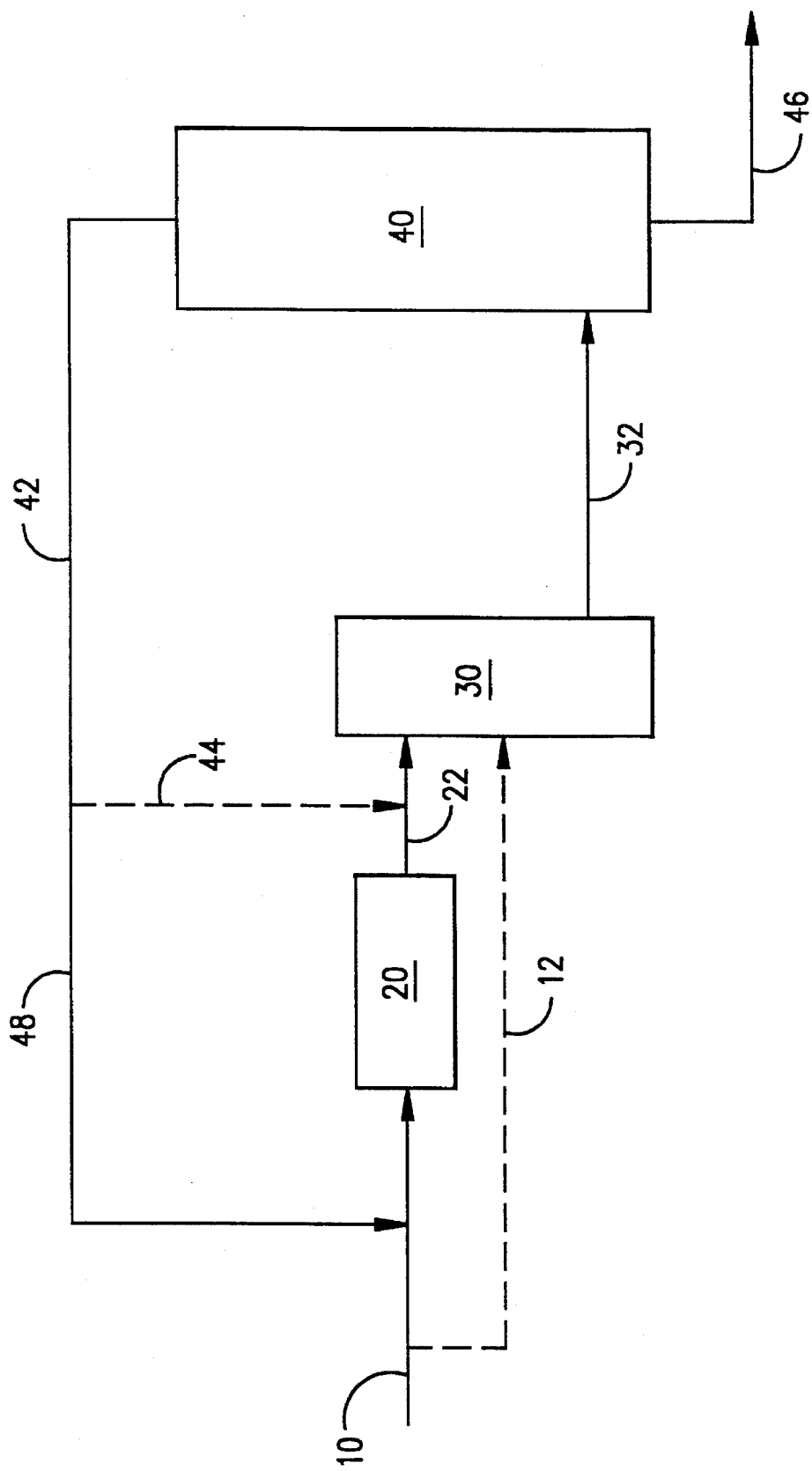

In one aspect, the present invention relates to a process for upgrading hydrocarbon feedstock comprising the steps of:

(i) recovering a $C_4$-rich aliphatic stream from a catalytic cracking process;

(ii) contacting said $C_4$-rich aliphatic stream with an isomerization catalyst comprising a zeolite sorbing 30 to 55 mg n-hexane at 90° C., 83 torr, and 15 to 40 mg 3-methylpentane at 90° C., 90 torr, per g dry zeolite in the hydrogen form in a first reaction stage to selectively isomerize $C_4$ n-olefins to $C_4$ isoolefins; and (iii) contacting in a second reaction stage the product stream from said first reaction stage with a solid acid alkylation catalyst selected from the group consisting of MCM-36 and MCM-49, as described herein and zeolites having a Constraint Index of less than or equal to about 2, to produce isoparaffinic alkylate gasoline.

In another aspect, the present invention relates to a process for upgrading hydrocarbon feedstock comprising the steps of:

(a) contacting a $C_4$-rich aliphatic stream containing isoparaffins and linear olefins with an isomerization catalyst comprising a zeolite sorbing 30 to 55 mg n-hexane at 90° C., 83 torr, and 15 to 40 mg 3-methylpentane at 90° C., 90 torr, per g dry zeolite in the hydrogen form in a first reaction stage to selectively isomerize linear butenes to isobutene;

(b) contacting the effluent from said first reaction stage containing isobutane, linear butenes, and isobutene with a solid acid alkylation catalyst selected from the group consisting of MCM-36 and MCM-49, as described herein and zeolites having a Constraint Index of less than or equal to about 2 in a second reaction stage, under conditions which selectively convert said isobutane and isobutene to isoparaffinic alkylate gasoline;

(c) fractioning said second reaction stage effluent containing isoparaffinic alkylate gasoline, unreacted isobutane and unreacted linear butenes to obtain isoparaffinic alkylate gasoline and an overhead comprising unreacted isobutane and linear butenes; and (d) recycling said overhead to step (a) or (b).

The effectiveness of solid acids such as zeolites in alkylation is known. Although these catalysts, e.g., rare earth-containing zeolite Y, are highly active for short periods of time, their activity falls rapidly in a matter of several hours. This results in very short cycle lengths and the catalyst requires frequent regenerations. As a result, the amount of alkylate produced per cycle per unit mass of catalyst is extremely small, rendering alkylation processes based on such catalysts economically unattractive. U.S. Pat. No. 5,258,569 to Chu et al. discloses an improved process wherein MCM-36 is used as alkylation catalyst resulting in substantially increased cycle length compared to rare earth-exchanged zeolite Y catalyst. However, where linear butenes are present in the alkylate feed, the trimethylpentane/dimethylhexane ratio (TMP/DMH) in the C8 fraction is significantly lower (2.0 to 2.5) than that obtained with HF and $H_2SO_4$ based alkylation processes, resulting in alkylate product of lower octane.

It has now been discovered that the TMP/DMH ratio in the C8 fraction of the alkylate can be significantly increased if the linear butenes in the alkylate feed are isomerized to isobutene prior to alkylation. Furthermore, the present invention takes advantage of isobutene's greater reactivity as compared to linear butenes in alkylation, allowing the process to be operated at significantly higher olefin space velocity, thereby increasing the economic viability of a solid catalyst based alkylation process.

Selective Isomerization

The first step of the process of the present invention converts a linear olefin-containing hydrocarbon feedstream to an iso-olefin rich product at high levels of conversion and high iso-olefin selectivity over a constrained medium-pore zeolite catalyst under skeletal isomerization conditions. Such conditions comprise temperatures between about 250° and 750° C., weight hourly space velocities (WHSV) based on linear olefins in said feedstock between 0.1 and 500 WHSV, linear olefin partial pressures between 12 and 500 kPa, and conversion levels of linear olefins at least 20 weight percent.

The skeletal isomerization reaction of the present invention is carried out at temperatures between 250° and 750° C.; weight hourly space velocity based on linear olefin in the feed between 0.1 and 500 WHSV; and linear olefin partial pressure between 12 and 500 kPa. The preferred conditions are temperatures between 325° and 600° C., more preferably between 350° and 550° C., WHSV between 0.5 and 200, more preferably between 1 and 50; and a linear olefin partial pressure between 30 and 300 kPa, more preferably between 50 and 150 kPa. Under these conditions the conversion of linear olefin, e.g., n-butene, can be at least 20%, preferably at least 35% and more preferably at least 45%. The selectivity to iso-olefin, e.g., isobutene, is at least 75%, preferably at least 85%, 90%, or even 95%.

The present invention is especially suited to processes carried out at high linear olefin to iso-olefin selectivity, e.g., at least 60% at relatively low conversion temperatures and high linear olefin partial pressures. Such processes can maintain selectivities of at least 75, 85 or 95% at a conversion temperature less than or equal to 550, 450, 400 or even 350° C., and linear olefin partial pressures above 2 psia (14 kPa), e.g. above 5 psia (34 kPa). Such processes can be carried out at an overall conversion of linear olefins of at least 30, 35, 40, or 45 wt % or higher.

Preferred feedstreams include $C_4$ or $C_4+$ hydrocarbon feedstreams. Linear olefins suited to use in the present invention may be derived from a fresh feedstream, preferably comprising n-butenes, or from the effluent of an iso-olefin etherification reactor which employs alkanol and $C_4$ or $C_4+$ hydrocarbon feedstock. Typical hydrocarbon feedstock materials for the isomerization step of the present invention include olefinic streams, such as cracking process light gas containing butene isomers in mixture with substantial amounts of paraffins including n-butane and isobutane. The $C_4$ components usually contain a major amount of unsaturated compounds, such as 10–40% isobutene, 20–55% linear butenes, and small amounts of butadiene.

Isomerization Catalysts

The preferred isomerization catalysts, exemplified by ZSM-22, ZSM-23, and ZSM-35, are members of a unique class of zeolites. They have channels described by 10-membered rings of T (=Si or Al) or oxygen atoms, i.e., they are intermediate pore zeolites, distinct from small pore 8-ring or large pore 12-ring zeolites. They differ, however, from other intermediate pore 10-ring zeolites, such as ZSM-5, ZSM-11, ZSM-57 or stilbite, in having a smaller 10-ring channel. If the crystal structure (and hence pore system) is known, a convenient measure of the channel cross-section is given by the product of the dimensions (in Angstrom units) of the two major axes of the pores. These dimensions are listed in the "Atlas of Zeolite Structure Types" by W. M. Meier and D. H. Olson, Butterworths, publisher, Second Edition, 1987. The values of this product, termed the Pore Size Index, are listed in Table A.

TABLE A

| | | Pore Size Index | | |
|---|---|---|---|---|
| Type | Largest Ring Size | Zeolite | Axes of Largest Channel, Å | Pore Size Index |
| 1 | 8 | Chabazite | 3.8 × 3.8 | 14.4 |
| | | Erionite | 3.6 × 5.1 | 18.4 |
| | | Linde A | 4.1 × 4.1 | 16.8 |
| 2 | 10 | ZSM-22 | 4.4 × 5.5 | 24.2 |
| | | ZSM-23 | 4.5 × 5.2 | 23.4 |
| | | ZSM-35 | 4.2 × 5.4 | 22.7 |
| | | ALPO-11 | 3.9 × 6.3 | 24.6 |
| 3 | 10 | ZSM-5 | 5.3 × 5.6 | 29.1 |
| | | ZSM-11 | 5.3 × 5.4 | 28.6 |
| | | Stilbite | 4.9 × 6.1 | 29.9 |
| | | ZSM-57 (10) | 5.1 × 5.8 | 29.6 |
| 4 | 12 | ZSM-12 | 5.5 × 5.9 | 32.4 |
| | | Mordenite | 6.5 × 7.0 | 45.5 |
| | | Beta (C-56) | 6.2 × 7.7 | 47.7 |
| | | Linde-L | 7.1 × 7.1 | 50.4 |
| | | Mazzite (ZSM-4) | 7.4 × 7.4 | 54.8 |
| | | $ALPO_4$-5 | 7.3 × 7.3 | 53.3 |

It can be seen that small pore, eight-ring zeolites have a Pore Size Index below about 17, the intermediate pore, 10-ring zeolites of about 22–30, and large pore, 12-ring zeolites above about 32. It is also apparent, that the 10-ring zeolites are grouped in two distinct classes; Type 2 with a Pore Size Index between about 22.7 and 24.6, and more broadly between about 20 and 26, and Type 3 with a Pore Size Index between 28.6 and 29.9, or more broadly, between about 28 and 31.

The zeolite useful for this invention are those of Type 2 with a Pore Size Index of 20–26.

Alternatively, these zeolites can be distinguished from Type 1 and Type 3 zeolites by their sorption characteristics. Equilibrium sorption data are listed in Table B below. While both Type 2 and Type 3 zeolites sorb more than about 40 mg n-hexane per gram zeolite, the Type 2 zeolites sorb less than 40 mg 3-methylpentane under the conditions specified, in contrast to Type 3 zeolites. Small pore, 8-ring zeolites sorb less than 15 mg of 3-methylpentane per gram of zeolite.

The equilibrium sorption are obtained most conveniently in a thermogravimetric balance by passing a stream of inert gas such as helium containing the hydrocarbon with the indicated partial pressure over the dried zeolite sample held at 90° C. for a time sufficient to obtain a constant weight.

This method of characterizing the Type 2 zeolites has the advantage that it can be applied to new zeolites whose crystal structure has not yet been determined. For mixtures of zeolites with amorphous material or for poorly crystallized samples, the numbers apply only to the crystalline portion.

Thus, zeolites useful for the isomerization step of the present invention sorb 30 to 55 mg n-hexane and 15 to 40 mg 3-methylpentane per g dry zeolite in the hydrogen form.

TABLE B

Equilibrium Sorption Data of Medium Pore Zeolites

| | | Amount sorbed, mg per g zeolite | |
| --- | --- | --- | --- |
| Type | Zeolite | n-Hexane[a] | 3-Methylpentane[b] |
| 2 | ZSM-22 | 40 | 20 |
| | ZSM-23 | 45 | 25 |
| | ZSM-35 | 50 | 25 |
| 3 | ZSM-5 | 103 | 61 |
| | ZSM-12 | 52 | 58 |
| | ZSM-57 | 60 | 70 |
| | MCM-22 | 89 | 79 |

[a] at 90° C., 83 torr n-hexane
[b] at 90° C., 90 torr 3-methylpentane

ZSM-22 is more particularly described in U.S. Pat. No. 4,556,477, the entire contents of which are incorporated herein by reference. ZSM-22 and its preparation in microcrystalline form using ethylpyridinium as directing agent are described in U.S. Pat. No. 4,481,177 to Valyocsik, the entire contents of which are incorporated herein by reference. For present purposes, "ZSM-22" is considered equivalent to its isotypes, which include Theta-1 (S. A. I. Barri, G. W. Smith, D. White and D. Young, Nature 312, 533 (1984), R. M. Highcock, G. W. Smith and D. Wood, Acta Cryst. C41, 1391 (1985); ISI-1 (T. Kozo and K. Noboru, European Patent Application 170,003 (1986)); KZ-2 (L. M. Parker and D. M. Bibby, Zeolites 3, 8 (1983)); and NU-10 (A. Araya and B. M. Lowe, Zeolites 4, 280 (1984)).

ZSM-23 is more particularly described in U.S. Pat. No. 4,076,842, the entire contents of which are incorporated herein by reference. For purposes of the present invention, ZSM-22 is considered to include its isotypes, e.g., EU-13, ISI-4, and KZ-1.

ZSM-35 and methods for its synthesis are taught in U.S. Pat. Nos. 4,016,245 to Plank et al., 4,017,195 to Rollman, 4,584,286 to Valyocsik, 4,925,548 to Rubin, and 5,174,980 to Hellring et al., which patents are incorporated by reference as if set forth at length herein. For purposes of the present invention, ZSM-35 is considered to include its isotypes, e.g., ferrierite, FU-9, ISI-6, NU-23, and Sr-D.

The zeolite catalyst used is preferably at least partly in the hydrogen form, e.g., HZSM-22, HZSM-23, or HZSM-35. Other metals or cations thereof, e.g. rare earth cations, may also be present. When the zeolites are prepared in the presence of organic cations, they may be quite inactive possibly because the intracrystalline free space is occupied by the organic cations from the forming solution. The zeolite may be activated by heating in an inert or oxidative atmosphere to remove the organic cations, e.g. by heating at over 500° C. for 1 hour or more. The hydrogen form can then be obtained by base exchange with ammonium salts followed by calcination, e.g. at 500° C. in air.

The catalysts employed in the present invention may also contain divalent or trivalent metal cations, preferably in amounts ranging from 0 to 3 wt %, more preferably from 0 to 2 wt %.

The metal may be incorporated into the catalyst by any suitable method such as impregnation or exchange onto the zeolite. The metal may be incorporated in the form of a cationic, anionic or a neutral complex, such as $Pt(NH_3)_4^{2+}$, and cationic complexes of this type are found convenient for exchanging metals onto a zeolite. Anionic complexes are also useful for impregnating metals into the zeolites.

Among the divalent metals suited to incorporation into the catalyst are those of Group IIA, e.g., Mg, Ca and Sr. Suitable trivalent metals include Fe, Al and the lanthanides. Included among the suitable divalent and trivalent metals are the Group VIIIA metals of which the noble metals such as Pd, Pt, Rh and Ru are believed particularly suited to use in the present invention. Among the foregoing metals are those which exhibit hydrogenation ability. Incorporation of hydrogenation metals is particularly useful in carrying out simultaneous butene isomerization and hydrogenation of dienes, e.g. butadiene, or alkynes such as acetylene.

It is generally desirable to incorporate the zeolite with another material resistant to the temperatures and other conditions employed in organic conversion processes. Such matrix materials include active and inactive materials and synthetic or naturally occurring zeolites as well as inorganic materials such as clays, silica and/or metal oxides. The latter may be either naturally occurring or in the form of gelatinous precipitates, sols or gels including mixtures of silica and metal oxides. Use of a material in conjunction with the zeolite, i.e., combined therewith, which is active, tends to improve the conversion and/or selectivity of the catalyst in certain organic conversion processes. However, for present purposes, inactive materials of low acidity such as silica or zirconia are preferred in that they prevent unwanted polymerization reactions engendered by more active materials such as alumina. Inactive materials can also suitably serve as diluents to control the amount of conversion in a given process so that products can be obtained economically and orderly without employing other means for controlling the rate of reaction.

Frequently, zeolite materials have been incorporated into naturally occurring clays, e.g. bentonite and kaolin. These materials, i.e. clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with the zeolite catalyst include the montmorillonite and kaolin family, which families include the sub-bentonites, and the kaolins commonly known as Dixie, McNamee, Georgia and Florida clays or others in which the main mineral constituents is halloysite, kaolinite, dickite, nacrite, or anauxite. Such clays can be used in the raw state as originally mined or initially subjected to calcination, acid treatment or chemical modification.

In addition to the foregoing materials, the zeolite can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

As noted above, of all the foregoing materials, silica is preferred as the matrix material owing to its relative inertness for catalytic polymerization reactions which are preferably minimized in the isomerization step of the present process. The relative proportions of finely divided zeolite and inorganic oxide gel matrix vary widely with the zeolite content ranging from about 5 to about 98 percent by weight of the composite.

The regeneration of spent zeolite catalyst used in the isomerization reaction is carried out oxidatively or hydrogenatively employing procedures known in the art. The catalyst of the present invention can be readily reactivated without significantly reducing selectivity for 2-olefins by exposing it to hydrogen for a suitable period, e.g., overnight, and temperature to effect reactivation. For example, the deactivated catalyst is heated in a flowing stream of hydrogen-containing gas to a temperature of 250° C. during 1 hour, and kept at 250° C. for 4 hours. Alternatively, the deactivated catalyst is heated to 350° C. in a flowing stream of inert gas such as nitrogen which contains 0.5% $O_2$ until the major exothermic temperature rise has subsided; the oxygen content is then increased stepwise to 1%, 3%, and finally to about 20%, and the temperature increased to 450° C. and held there for 6 hours.

In order to obtain desired linear olefin skeletal isomerization activity/selectivity, the catalyst useful in the present invention is preferably in the hydrogen form.

U.S. Pat. No. 5,157,194 to Rahmim et al. teaches the selective skeletal isomerization of n-butenes to i-butene in the presence of zeolite ZSM-22, and is incorporated by reference as if set forth at length herein.

Solid-Catalyzed Alkylation

The operating temperature of the alkylation stage of the present invention can extend over a fairly broad range, e.g., from about +25° to about 400° C., and is preferably within the range of from about 75° C. to about 200° C. The practical upper operating temperature will often be dictated by the need to avoid an undue occurrence of undesirable side reactions.

The pressures employed in the alkylation stage of the present process can extend over a considerably wide range, e.g., from subatmospheric pressure to about 5000 psig, and preferably from atmospheric pressure to about 2000 psig.

The amount of solid alkylation catalyst used in the alkylation stage can be varied over relatively wide limits. In general, the amount of solid alkylation catalyst as measured by the weight hourly space velocity (WHSV) based on olefin can range from about 0.01 to about 100 $hr^{-1}$, preferably from 0.04 to 5 $hr^{-1}$. It will, of course, be realized by those skilled in the art that the amount of catalyst selected for a particular reaction will be determined by several variables including the reactants involved as well as the nature of the catalyst and the operating conditions employed.

In general, the mole ratio of total isoparaffin to total olefin alkylating agent in the intermediate hydrocarbon stream flowing from the etherification unit to the alkylation reaction stage can be as low as about 5:1, preferably at least about 15:1, more preferably greater than about 20:1. Suitable ranges include 5:1 to 50:1, say 5:1 to 15:1.

The isoparaffin and/or olefin reactants can be in the vapor phase, the liquid phase and/or a supercritical state and can be neat, i.e., free from intentional admixture of dilution with other material, or the reactants can be brought into contact with the catalyst composition with the aid of carrier gases or diluents such as, for example, hydrogen or nitrogen. The reactants also may optionally be introduced to the alkylation reaction zone together with one or more other reactive materials which may serve to enhance the overall conversion operation. Thus, for example, relatively small quantities of hydrogen and/or hydrogen donors can be present in the reaction zone.

The molar ratio of n-$C_4$ olefins to iso-$C_4$ olefins at the alkylation reaction stage inlet is less than 2.0, preferably less than 1.5, say 0.8 to 1.5.

In a preferred embodiment, the alkylation stage is maintained at conditions of sufficiently low severity, such that the linear butenes present in the feed become unreactive, resulting in selective alkylation of isobutane with isobutene. Such trimethylpentane-selective conditions include temperatures from 50° to 300° C., and is preferably within the range of from 75° C. to 200° C., pressures from atmospheric to 2000 psig, preferably from 50 to 1000 psig, and weight hourly space velocity (WHSV) based on olefin ranging from 0.01 to 100 $hr^{-1}$, preferably from 0.1 to 5 $hr^{-1}$. The unconverted linear butenes can be recovered from the alkylate product and recycled, along with recovered isobutane, to the olefin skeletal isomerization reactor. In this manner, the alkylation reactor effectively separates linear butenes from isobutene for recycle to the isomerization reactor. Alternatively, the recovered isobutane and linear butenes can be recycled to the alkylation reactor as necessary to control isoparaffin to olefin mole ratio. In another embodiment, the $C_4$-rich aliphatic stream, or a portion thereof, from a catalytic cracking process, e.g., FCC effluent, can be routed directly to the alkylation reactor, bypassing the isomerization reactor. This can serve to effect removal of iso-olefins, e.g., isobutene, resulting in recycle feed to the isomerization reactor which is of higher linear olefin content than that obtained directly from catalytic cracking processes. Utilizing a feed to the isomerization reactor of higher linear olefin content and lower isoolefin content can serve to enhance the efficiency of the isomerization stage.

The integrated process of the present invention can produce isoparaffinic alkylate gasoline having a higher trimethylpentane to dimethylhexane ratio than that obtained in the absence of the skeletal isomerization step. In one preferred embodiment, the trimethylpentane to dimethylhexane ratio is greater than 2.5, preferably greater than 4.

The alkylation stage of the present invention can be carried out as a batch-type, semi-continuous or continuous operation utilizing a fixed or moving bed of the solid alkylation catalyst component. A preferred embodiment entails use of a catalyst zone wherein the hydrocarbon charge is passed concurrently or countercurrently through a moving bed of particle-form solid alkylation catalyst. The latter, after use, is conducted to a regeneration zone where coke is removed, e.g., by burning in an oxygen-containing atmosphere (such as air) at elevated temperature or by extracting with a solvent, after which the regenerated catalyst is recycled to the conversion zone for further contact with the organic reactants.

Useful catalysts for the alkylation step of the invention generally include the layered material MCM-36, as described in U.S. Pat. No. 5,258,569 to Chu et al., incorporated herein by reference, the synthetic porous material MCM-49 as described in U.S. Pat. No. 5,236,575 to Bennett et al., incorporated herein by reference, as well as zeolitic materials characterized by a Constraint Index of less than or equal to about 2. Members of the class of zeolites having a Constraint Index of less than or equal to about 2 include zeolite Beta, zeolite X, zeolite Y, mordenite, and ZSM-12, merely to name a few.

The layers of the MCM-36 may have a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 5, usually from about 10 to about 150, more usually from about 10 to about 60, and even more usually from about 10 to about 40.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical Number zeolite materials and is incorporated by reference as if set forth at length herein.

Particular process configurations and variations may be arrived at by substituting at least one of the foregoing solid alkylation catalysts for the MCM-22 catalyst as described in the aforementioned U.S. Pat. Nos. 4,992,615; 5,012,033; and 5,073,665.

The examples which follow illustrate the invention without restricting it in any way.

EXAMPLE 1

Preparation of ZSM-35

1.18 parts of aluminum sulfate (17.2% $Al_2O_3$) were added to a solution containing 9.42 parts $H_2O$ and 1.38 parts of 50% NaOH solution in an autoclave. 0.03 parts of ZSM-35 seeds and 3.20 parts of Hi-Sil precipitated silica were added with agitation, followed by 1.0 part of pyrrolidine.

The reaction mixture had the following composition, in mole ratios:

| | |
|---|---|
| $SiO_2/Al_2O_3$ | 21.5 |
| $OH^-/SiO_2$ | 0.11 |
| $H_2O/Al_2O_3$ | 13.5 |
| $R/Al_2O_3$ | 6.45 | where R=pyrrolidine. The mixture was crystallized at 105° C. for 74 hours with stirring. The ZSM-35 product was filtered, washed with deionized water, and dried at 120° C.

The chemical composition of the product was, in weight percent:

| | |
|---|---|
| $SiO_2$ | 76.7 |
| $Al_2O_3$ | 6.4 |
| Na | 0.84 |
| C | 7.26 |
| N | 2.03 |
| Ash @ 1000° C. | 85.5 | with a silica/alumina ratio for the product, in moles, of 20.3/1.

Scanning electron microscopy and transmission electron microscopy indicate the ZSM-35 crystals have platelet morphology with a broad distribution of crystal sizes having the largest dimension of up to 0.05 to 0.1 micron.

EXAMPLE 2

Preparation of Silica-Bound HZSM-35

A catalyst was prepared by dry mixing the as-synthesized ZSM-35 of Example 1 with precipitated silica. Colloidal silica, in proportion to give 65% ZSM-35/35% silica after calcination, and water were added to the dry mix to obtain an extrudable mull. The mull was extruded to 1/16 inch (1.6 mm) diameter, dried at 120° C., calcined in nitrogen for three hours at 538° C., and then in air for 6 hours at 538° C. The extrudate was exchanged two times with 1N $NH_4NO_3$ solution at room temperature, dried at 120° C. and calcined in air for 3 hours at 538° C. The total pore volume of this catalyst was 0.55 cc/g and $300^+$ angstrom pore volume was measured as 0.04 cc/g.

EXAMPLE 3

Isomerization of 1-Butene over $ZSM-35/SiO_2$

The $ZSM-35/SiO_2$ of Example 2 was used in 1-butene skeletal isomerization reactions carried out at 401° C., 34 WHSV (based on HC), 30 psia, using a 1:1 vol/vol nitrogen/1-butene feed. Additional conditions of the run and the product composition are set out below in Table 1.

TABLE 1

| WHSV: | 34 |
|---|---|
| Temperature (C): | 400 |
| Pressure (PSIA): | 30 |
| HOS: | 20 |
| N2/1-Butene in Feed: | 1 |
| COMPOUND | % IN PROD |
| Methane | 0.00 |
| Ethane | 0.04 |
| Ethylene | 0.14 |
| Propane | 0.00 |
| Propylene | 0.68 |
| Isobutane | 0.00 |
| N-Butane | 0.66 |
| Trans-2-Butene | 26.50 |
| 1-Butene | 12.39 |
| Isobutylene | 36.02 |
| Cis-2-Butene | 22.36 |
| Total C5- | 98.80 |
| 3-Methyl-1-Butene | 0.00 |
| Trans-2-Pentene | 0.12 |
| 2-Methyl-2-Butene | 0.60 |
| 1-Pentene | 0.00 |
| 2-Methyl-1-Butene | 0.20 |
| Cis-2-Pentene | 0.15 |
| Carbon 6+ | 0.13 |
| Total Pentenes | 1.07 |
| Isoamylenes | 0.80 |
| % Conversion | 38.75 |
| Sel. for Isobutene (%) | 92.96 |

EXAMPLES 4 TO 6

Examples 4 to 6 demonstrate the effect of olefin feed concentration on alkylate quality, expressed in terms of the ratio of trimethylpentane to dimethylhexane (T/D), and on alkylate selectivity in terms of the relative amounts of $C_8$ and $C_9+$ produced. Increasing the isobutene content of the feed improved alkylate quality (as indicated by the increase in T/D from Example 4 through Example 6). The improved T/D ratio was somewhat offset by the decreasing $C_8$ fraction. This loss in $C_8$ alkylate was attributable to increased selectivity toward the less-desired $C_5$–$C_7$ and $C_9+$ fractions.

TABLE 2

Conditions: 300° F., 700 psig ~ 0.1 olefin WHSV, I/O (feed) = 10/1,
Recycle ratio = 5:1, continuous operation, fixed bed reactor.
Catalyst: MCM-36 composited (65/35 wt./wt.) in an $Al_2O_3$ binder, extruded and crushed to mesh 30/60.

| | Example No. | | |
|---|---|---|---|
| | 4 | 5 | 6 |
| FEED OLEFIN: | | | |
| 2-Butene (%) | 100 | 50 | 0 |
| Isobutene (%) | 0 | 50 | 100 |
| INTERNAL I/O ACHIEVED | 28 | 53 | 53 |
| OLEFIN CONVERSION (wt. %) | 81 | 98 | 99 |
| $C_5$+COMPOSITION (wt. %) | | | |
| $C_5$–$C_7$ | 12 | 23 | 24 |
| $C_8$ | 60 | 36 | 28 |
| $C_9$+ | 29 | 41 | 48 |
| $C_8$ QUALITY | | | |
| T/D | 1.9 | 3.6 | 6.2 |

EXAMPLES 7 AND 8

Examples 7 and 8 compared isoparaffin/n-olefin alkylation (Example 7) with isoparaffin/i-olefin alkylation (Example 8) in the presence of the solid alkylation catalyst MCM-36. The pilot unit evaluations were carried out at 700 psig and 300° F. using the desired feed with a 50/1 ratio of isobutane/olefin at 0.1 olefin WHSV. The data contained in Table 3 clearly demonstrate that the TMP/DMH ratio is increased when isobutene is the olefin component in the feed as compared to 2-butene. The activity as measured by olefin conversion is also higher at 0.2 hr$^{-1}$ olefin WHSV. While the C9+ and C5–C7 yields are also higher with the isobutene containing feed, it is believed the product distribution can be shifted towards greater C8 levels via process designs which give high internal isoparaffin/olefin ratios.

TABLE 3

EXAMPLES 7 AND 8

Conditions: 300° F., 700 psig ~ 0.2 hr.$^{-1}$ olefin WHSV, I/O = (feed) 50/1, no recycle.
Catalyst: MCM-36 composited (65/35 wt./wt.) in an $Al_2O3$ binder, pelletized and crushed to mesh 30/60.

| | Example No. | |
|---|---|---|
| | 7<br>2-Butene | 8<br>Isobutene |
| Olefin | | |
| Olefin Conv, wt % | 96.7 | 98.3 |
| TOS (days) | 10–11 | 13–15 |
| C4= Conv. (Wt %) | 96.7 | 98.3 |
| $C_5$+ Composition, wt % | | |
| $C_5$–$C_7$ | 22 | 36 |
| $C_8$ | 60 | 28 |
| $C_9$+ | 18 | 36 |
| $C_8$ QUALITY T/D | 2.3 | 4.9 |

Process Flow Schematic

A preferred embodiment of the invention is illustrated in the Figure. Referring to the Figure, a light aliphatic feedstream 10 principally comprising $C_4$ olefins and isobutane from a fluid catalytic cracking process is preferably mixed with recycled isobutane and linear butenes (from lines 42 and 48) and introduced to an isomerization reaction zone 20 containing a solid catalyst comprising ZSM-35 to isomerize at least a portion of the feed n-butenes to isobutylene. The product stream 22 from isomerization reaction zone 20 enters alkylation reaction zone 30 which contains a solid alkylation catalyst having the structure of MCM-36 as defined herein. In one embodiment, particularly where the light aliphatic feedstream from FCC contains at least 15 wt %, say 25 wt % isobutylene, a portion of said feedstream can be routed directly through line 12 to the alkylation reaction zone 30, bypassing the isomerization reaction zone 20. In another embodiment, recycled isobutane and linear butenes are recycled to alkylation reaction zone 30 via line 44. The alkylation reaction stage effluent 32 contains alkylated product together with unreacted isobutane and linear butenes and flows to distillation tower 40 which separates an isobutane- and linear butene-rich stream 42 from the alkylate product 46. The isobutane- and linear butene-rich stream is then recycled through lines 42 and 44 as described above. While it is preferred that a portion of the isobutane/linear butenes from line 42 be recycled through line 48 to line 10 for the purpose, inter alia, of controlling olefin partial pressure in the isomerization reaction stage 20, the recycled isobutane/linear butenes from line 42 can flow through line 44 to line 22 directly to alkylation reaction zone 30. However, recycling directly to the skeletal isomerization zone utilizes the alkylation reactor to effectively separate linear butenes from isobutene, thereby avoiding the capital and operating expense associated with fractionating C4 isomers.

While the invention has been described by reference to specific embodiments, there is no intent to limit the scope of the invention except as described in the following claims.

What is claimed is:

1. A process for upgrading hydrocarbon feedstock comprising the steps of:

(a) recovering a $C_4$-rich aliphatic stream from a catalytic cracking process;

(b) contacting said $C_4$-rich aliphatic stream with an isomerization catalyst comprising a zeolite sorbing 30 to 55 mg n-hexane at 90° C., 83 torr, and 15 to 40 mg 3-methylpentane at 90° C., 90 torr, per g dry zeolite in the hydrogen form in a first reaction stage to selectively isomerize $C_4$ n-olefins to $C_4$ isoolefins;

(c) contacting in a second reaction stage the product stream from said first reaction stage with a solid acid alkylation catalyst selected from the group consisting of MCM-36 and MCM-49, as described herein and zeolites having a Constraint Index of less than or equal to about 2, to produce isoparaffinic alkylate gasoline.

2. The process of claim 1 wherein said isomerization catalyst has the structure of at least one zeolite selected from the group consisting of ZSM-22, ZSM-23 and ZSM-35.

3. A process according to claim 1, wherein said solid alkylation catalyst comprises MCM-36 as defined herein, and the layers of said MCM-36 have a composition comprising the molar relationship $$X_2O_3:(n)YO_2,$$

wherein n is at least about 5, X is a trivalent element and Y is a tetravalent element.

4. A process according to claim 3, wherein X is selected from the group consisting of aluminum, boron, gallium and combinations thereof and Y is selected from the group consisting of silicon, germanium and combinations thereof.

5. A process according to claim 3, wherein X comprises aluminum and Y comprises silicon.

6. A process according to claim 1, wherein the reaction is carried out under sufficient pressure to maintain at least one of the reactants in the liquid phase.

7. A process according to claim 1, wherein the mole ratio of total isoparaffin to total olefin in the intermediate hydrocarbon feedstream charged to step (c) is from about 5:1 to about 50:1.

8. A process according to claim 1, wherein the mole ratio of total isoparaffin to total olefin in the intermediate hydrocarbon feedstream charged to step (c) is from about 5:1 to about 15:1.

9. A process according to claim 1, wherein alkylation reaction temperature is from about +25° C. to about 400° C., pressure is from below atmospheric to about 5000 psig and weight hourly space velocity based on olefin is from about 0.01 to 100 $hr^{-1}$.

10. A process according to claim 1, wherein alkylation reaction temperature is from about 75° C. to about 200° C., pressure is from atmospheric to about 2000 psig and weight hourly space velocity of the olefin is from about 0.04 to about 5 $hr^{-1}$.

11. A process according to claim 1 wherein the alkylation reaction is carried out under trimethylpentane-selective conditions wherein the isobutane preferentially reacts with isobutene.

12. A process according to claim 11 wherein said trimethylpentane-selective conditions include temperatures from 75° to 200° C., pressures from 50 to 1000 psig, and weight hourly space velocity (WHSV) based on olefin ranging from 0.1 to 5 $hr^{-1}$.

13. A process according to claim 1 conducted in the presence of hydrogen and/or a hydrogen donor.

14. A process according to claim 1, wherein said $C_4$-rich aliphatic stream contains isobutane, isobutene, 2-butenes, and 1-butene.

15. A process according to claim 1, wherein said isoparaffinic alkylate gasoline has a higher trimethylpentane to dimethylhexane ratio than that obtained in the absence of step (b).

16. A process according to claim 15 wherein said trimethylpentane to dimethylhexane ratio is greater than 2.5.

17. A process according to claim 15 wherein said trimethylpentane to dimethylhexane ratio is greater than 4.

18. A process according to claim 1 wherein at least a portion of said recovered $C_4$-rich aliphatic stream is directed to the second reaction stage contacted with said solid acid alkylation catalyst.

19. A process for upgrading hydrocarbon feedstock comprising the steps of:

(a) contacting a $C_4$-rich aliphatic stream containing isoparaffins and linear olefins with an isomerization catalyst comprising a zeolite sorbing 30 to 55 mg n-hexane at 90° C., 83 torr, and 15 to 40 mg 3-methylpentane at 90° C., 90 torr, per g dry zeolite in the hydrogen form in a first reaction stage to selectively isomerize linear butenes to isobutene;

(b) contacting the effluent from said first reaction stage containing isobutane, linear butenes, and isobutene with a solid acid alkylation catalyst selected from the group consisting of MCM-36 and MCM-49, as described herein and zeolites having a Constraint Index of less than or equal to about 2 in a second reaction stage, under conditions which selectively convert said isobutane and isobutene to isoparaffinic alkylate gasoline;

(c) fractioning said second reaction stage effluent containing isoparaffinic alkylate gasoline, unreacted isobutane and unreacted linear butenes to obtain isoparaffinic alkylate gasoline and an overhead comprising unreacted isobutane and linear butenes; and (d) recycling said overhead to step (a) or (b).

20. A process according to claim 19 wherein said overhead is recycled to step (a).

21. A process according to claim 19 wherein said overhead is recycled to step (b).

22. A process according to claim 19 wherein at least a portion of said $C_4$-rich aliphatic stream is directed to the second reaction stage and contacted with said solid acid alkylation catalyst.

* * * * *